(12) United States Patent
Smits et al.

(10) Patent No.: US 8,010,207 B2
(45) Date of Patent: Aug. 30, 2011

(54) IMPLANTABLE MEDICAL LEAD DESIGNS

(75) Inventors: Karel F. A. A. Smits, Munstergeleen (NL); Jean J. G. Rutten, Bocholtz (NL); Paul G. Adams, Munstergeleen (NL)

(73) Assignee: Medtronic, Inc., Minneapolis, MN (US)

( * ) Notice: Subject to any disclaimer, the term of this patent is extended or adjusted under 35 U.S.C. 154(b) by 79 days.

(21) Appl. No.: 10/420,110

(22) Filed: Apr. 21, 2003

(65) Prior Publication Data
US 2004/0088034 A1 May 6, 2004

Related U.S. Application Data

(60) Provisional application No. 60/422,955, filed on Oct. 31, 2002.

(51) Int. Cl.
*A61N 1/05* (2006.01)
(52) U.S. Cl. .................................................. 607/116
(58) Field of Classification Search .............. 607/2, 116, 607/122, 123, 126, 127, 128
See application file for complete search history.

(56) References Cited

U.S. PATENT DOCUMENTS

| | | | |
|---|---|---|---|
| 3,857,399 A | 12/1974 | Zacouto | |
| 4,057,067 A | 11/1977 | Lajos | 128/418 |
| 4,379,459 A | 4/1983 | Stein | |
| 4,394,866 A | 7/1983 | Hughes | 128/785 |
| 4,402,328 A | 9/1983 | Doring | 128/785 |
| 4,402,330 A | 9/1983 | Lindemans | 128/786 |
| 4,454,888 A | 6/1984 | Gold | 128/785 |
| 4,476,868 A | 10/1984 | Thompson | |
| 4,493,329 A | 1/1985 | Crawford et al. | |
| 4,627,439 A * | 12/1986 | Harris | 166/272.5 |
| 4,821,723 A | 4/1989 | Baker, Jr. et al. | |
| 4,899,750 A | 2/1990 | Ekwall | |
| 4,917,104 A | 4/1990 | Rebell | |
| 4,936,304 A | 6/1990 | Kresh et al. | |
| 4,972,848 A * | 11/1990 | Di Domenico et al. | 607/127 |
| 4,997,431 A | 3/1991 | Isner et al. | |
| 5,003,975 A | 4/1991 | Hafelfinger et al. | |
| 5,131,388 A | 7/1992 | Pless et al. | |
| 5,144,949 A | 9/1992 | Olson | |
| 5,158,078 A | 10/1992 | Bennett et al. | |
| 5,312,453 A | 5/1994 | Shelton et al. | |
| 5,314,430 A | 5/1994 | Bardy | 607/5 |
| 5,330,521 A * | 7/1994 | Cohen | 607/122 |
| 5,354,316 A | 10/1994 | Keimel | |
| 5,374,287 A | 12/1994 | Rubin | |

(Continued)

FOREIGN PATENT DOCUMENTS

WO WO 01/74443 A1 10/2001

*Primary Examiner* — Niketa I Patel
*Assistant Examiner* — Alyssa M Alter
(74) *Attorney, Agent, or Firm* — Reed A. Duthler; Stephen W. Bauer

(57) ABSTRACT

The invention is directed to medical leads for use with implantable medical devices. Various features of medical leads are described, many of which may be useful in a variety of different leads, e.g., used in a variety of different applications. In one embodiment, the invention provides a medical lead of varying stiffness characteristics. In another embodiment, the invention provides a medical lead having a semi-conical shaped distal tip that becomes wider at more distal tip locations. In either case, described lead features may be particularly useful for J-shaped lead configurations used for implantation in a patient's right atrium. Many other types of leads, however, could also benefit from various aspects of the invention.

11 Claims, 9 Drawing Sheets

U.S. PATENT DOCUMENTS

| | | | | |
|---|---|---|---|---|
| 5,456,707 | A | 10/1995 | Giele | |
| 5,484,445 | A | 1/1996 | Knuth | |
| 5,487,758 | A | 1/1996 | Hoegnelid et al. | |
| 5,514,173 | A | 5/1996 | Rebell et al. | |
| 5,522,876 | A | 6/1996 | Rusink | |
| 5,531,780 | A | 7/1996 | Vachon | |
| 5,531,783 | A | 7/1996 | Giele et al. | |
| 5,534,018 | A | 7/1996 | Wahlstrand et al. | |
| 5,545,186 | A | 8/1996 | Olson et al. | |
| 5,545,201 | A | 8/1996 | Helland et al. | |
| 5,545,206 | A | 8/1996 | Carson | |
| 5,545,207 | A | 8/1996 | Smits et al. | |
| 5,571,162 | A | 11/1996 | Lin | |
| 5,575,814 | A | 11/1996 | Giele et al. | |
| 5,597,224 | A | 1/1997 | Kobayashi | |
| 5,658,327 | A | 8/1997 | Altman et al. | |
| 5,683,446 | A | 11/1997 | Gates | |
| 5,683,447 | A | 11/1997 | Bush et al. | |
| 5,693,081 | A | 12/1997 | Fain et al. | |
| 5,716,391 | A | 2/1998 | Grandjean | |
| 5,716,392 | A | 2/1998 | Bourgeois et al. | |
| 5,728,140 | A | 3/1998 | Salo et al. | |
| 5,741,321 | A | 4/1998 | Brennen | |
| 5,755,767 | A | 5/1998 | Doan et al. | |
| 5,776,178 | A | * 7/1998 | Pohndorf et al. | 607/127 |
| 5,800,465 | A | 9/1998 | Thompson et al. | |
| 5,833,715 | A | 11/1998 | Vachon et al. | |
| 5,837,006 | A | 11/1998 | Ocel et al. | |
| 5,837,007 | A | 11/1998 | Altman et al. | |
| 5,851,227 | A | 12/1998 | Spehr | |
| 5,865,842 | A | 2/1999 | Knuth et al. | |
| 5,871,532 | A | 2/1999 | Schroeppel | |
| 5,876,431 | A | 3/1999 | Spehr et al. | |
| 5,902,331 | A | 5/1999 | Bonner et al. | |
| 5,948,015 | A | 9/1999 | Hess et al. | |
| 5,951,597 | A | 9/1999 | Westlund et al. | |
| 5,964,795 | A | 10/1999 | McVenes et al. | |
| 5,968,087 | A | 10/1999 | Hess et al. | |
| 5,991,667 | A | 11/1999 | Feith | |
| 6,006,122 | A | 12/1999 | Smits | |
| 6,010,526 | A | 1/2000 | Sandstrom et al. | |
| 6,040,620 | A | 3/2000 | Sugimoto et al. | |
| 6,049,736 | A | 4/2000 | Stewart et al. | |
| 6,055,457 | A | 4/2000 | Bonner | |
| 6,078,840 | A | 6/2000 | Stokes | |
| 6,083,216 | A | * 7/2000 | Fischer, Sr. | 604/530 |
| 6,097,986 | A | 8/2000 | Janke et al. | |
| 6,122,553 | A | 9/2000 | Ideker et al. | |
| 6,132,390 | A | 10/2000 | Cookston et al. | |
| 6,132,456 | A | 10/2000 | Sommer et al. | |
| 6,141,593 | A | * 10/2000 | Patag | 607/122 |
| 6,141,594 | A | 10/2000 | Flynn et al. | 607/127 |
| 6,152,954 | A | 11/2000 | Scheiner et al. | 607/123 |
| 6,185,464 | B1 | 2/2001 | Bonner et al. | |
| 6,212,434 | B1 | 4/2001 | Scheiner et al. | 607/123 |
| 6,263,249 | B1 | 7/2001 | Stewart et al. | |
| 6,263,250 | B1 | 7/2001 | Skinner | |
| 6,301,507 | B1 | 10/2001 | Bakels et al. | 607/122 |
| 6,304,786 | B1 | 10/2001 | Heil, Jr. et al. | |
| 6,321,102 | B1 | 11/2001 | Spehr et al. | |
| 6,321,104 | B1 | 11/2001 | Gielen et al. | |
| 6,321,122 | B1 | 11/2001 | Scheiner et al. | |
| 6,324,415 | B1 | 11/2001 | Spehr et al. | |
| 6,345,204 | B1 | 2/2002 | Scheiner et al. | 607/123 |
| 6,477,427 | B1 | * 11/2002 | Stolz et al. | 607/116 |
| 2003/0199962 | A1 | 10/2003 | Struble et al. | 607/126 |
| 2004/0088033 | A1 | 5/2004 | Smits et al. | |

\* cited by examiner

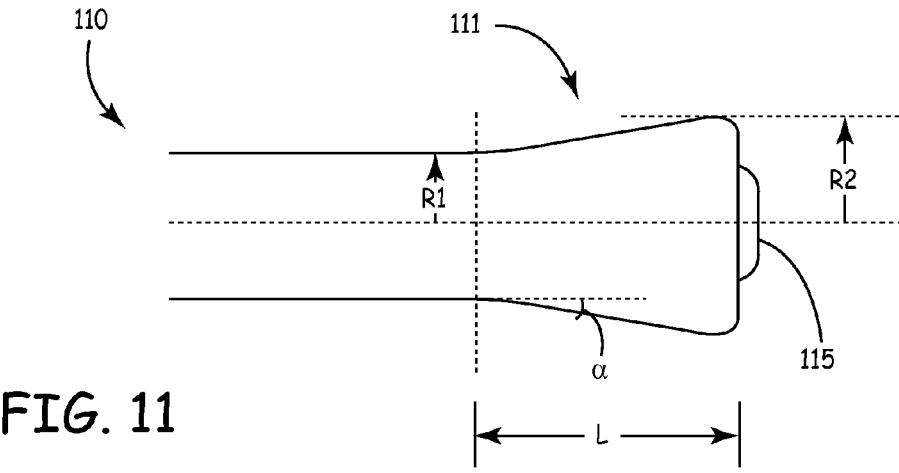
FIG. 11
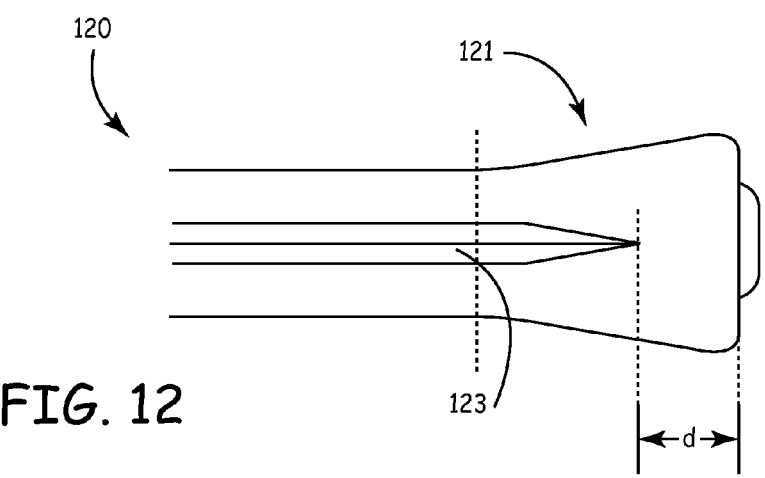
FIG. 12
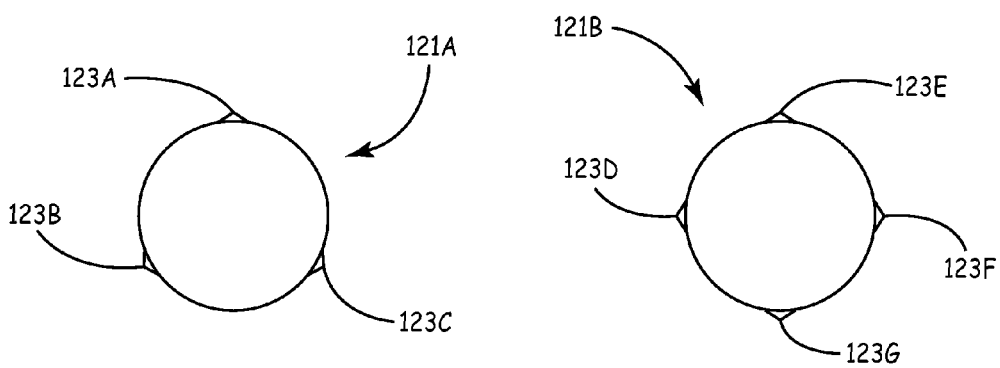
FIG. 13
FIG. 14

IMPLANTABLE MEDICAL LEAD DESIGNS

This application claims priority from U.S. Provisional Application Ser. No. 60/422,955, filed Oct. 31, 2002, the entire content of which is incorporated herein by reference.

FIELD OF THE INVENTION

The invention relates to medical devices and, more particularly, to implantable medical leads for use with implantable medical devices (IMDs).

BACKGROUND OF THE INVENTION

In the medical field, implantable leads are used with a wide variety of medical devices. For example, implantable leads are commonly used to form part of implantable cardiac pacemakers that provide therapeutic stimulation to the heart by delivering pacing, cardioversion or defibrillation pulses. The pulses can be delivered to the heart via electrodes disposed on the leads, e.g., typically near distal ends of the leads. In that case, the leads may position the electrodes with respect to various cardiac locations so that the pacemaker can deliver pulses to the appropriate locations. Leads are also used for sensing purposes, or both sensing and stimulation purposes.

In addition, implantable leads are used in neurological devices such as deep-brain stimulation devices, and spinal cord stimulation devices. For example, leads may be stereotactically probed into the brain to position electrodes for deep brain stimulation. Leads are also used with a wide variety of other medical devices including, for example, devices that provide muscular stimulation therapy, devices that sense chemical conditions in a patient's blood, gastric system stimulators, implantable nerve stimulators, implantable lower colon stimulators, e.g., in gracilonplasty applications, implantable drug or beneficial agent dispensers or pumps, implantable cardiac signal loops or other types of recorders or monitors, implantable gene therapy delivery devices, implantable incontinence prevention or monitoring devices, implantable insulin pumps or monitoring devices, and the like. In short, medical leads may be used for sensing purposes, stimulation purposes, drug delivery, and the like.

A number of challenges exist with respect to medical leads. In particular, new and improved lead designs are often needed to facilitate medical implantation to specific locations within a patient. For example, the stiffness characteristics of a medical lead may affect the ability to bend or conform a medical lead to a desired configuration. A stylet is often used to bend or form a distal region of the medical lead into a configuration that can allow for implantation of the lead tip into patient tissue at a desired location. As one example, J-shaped stylets may be inserted into a lumen of a medical lead to define a J-shaped configuration of a distal region of the medical lead once the distal region is inside a heart chamber. In that case, the distal tip of the lead may be implanted near the top of the right atrial chamber. Stiffness characteristics of the medical lead may affect the ability to achieve such a desired shape, however, and may also affect the shape of the medical lead following removal of the stylet.

Tissue fixation is another challenge relating to medical leads. In particular, a tip on the distal end of the medical lead may define certain shapes to improve fixation to tissue, and possibly harness the effects of fibrous tissue growth in order to anchor the lead tip in the tissue of a patient. For example, conventional leads commonly make use of distal tines to facilitate such anchoring in patient tissue. Distal tines, however, make lead removal much more traumatic to a patient because the tines can cause significant tissue damage upon removal from tissue. Moreover, the ability to adequately anchor a lead tip in tissue can also be complicated when the lead assumes different shapes, such as a J-shaped distal tip.

BRIEF SUMMARY OF THE INVENTION

The invention is directed to implantable medical leads for use with implantable medical devices. Various features of medical leads are described, many of which may be useful in a variety of different leads used in a variety of different applications. As one example, the features described herein may be particularly useful in leads designed for implantation in a patient's right atrium. In that case, the lead can be designed to facilitate formation of a J-shaped distal region following implantation of the lead in the patient's right atrium. A J-shaped stylet may be inserted through a lumen of the medical lead to form the J-shaped distal region.

In one embodiment, the invention provides a medical lead of varying stiffness characteristics. The features that facilitate the varying stiffness may be useful in a wide variety of applications, including specific applications in which the lead assumes a J-shaped distal region for implantation in a patient's right atrium. In that case, the distal region of the implanted lead may benefit from enhanced stiffness in order to ensure that the distal region maintains the J-shape following removal of a J-shaped stylet. In order to provide improved stiffness at one or more lead locations, a medical lead may comprise a first coiled portion including N filar(s), and a second coiled portion electrically coupled to the first coiled portion. The second coiled portion may include N+M filars to define increased stiffness of the second coiled portion relative to the first coiled portion, wherein N and M are positive integers.

In another embodiment, the invention provides a medical lead having semi-conical shaped distal tip that becomes wider at more distal tip locations. In other words, the distal tip tapers radially outward. Semi-conical distal tip features may find uses in a variety of lead applications, including specific applications in which the lead assumes a J-shaped distal region for implantation in a patient's right atrium. The semi-conical shaped tip may provide a structure that allows fibrous tissue growth to anchor the lead, but may be less aggressive than conventional tines, allowing removal without substantial tissue mutilation. Moreover, the semi-conical shape may harness an inherent spring force of a J-shaped lead configuration such that an axial force component of forces that counterbalance the inherent spring force can be used to force the lead tip against tissue of a patient's atrium.

For example, a medical lead may comprise a lead body defining a proximal end for attachment to a medical device and a distal end for implantation at a location in a patient. The medical lead may further comprise a semi-conical shaped tip at the distal end, the semi-conical shaped tip becoming wider at locations further from the proximal end.

In other embodiments the invention may be directed to an implantable medical device (IMD) including a housing to house circuitry, and a medical lead electrically coupled to the circuitry. The medical lead may include the features mentioned above, such as first and second coiled portions to allow for variable stiffness of a first portion relative to a second portion, or a semi-conical shaped distal tip to improve fixation of the lead tip to tissue and possibly harness spring forces in a useful way. In some cases, the lead may include both the first and second coiled portions to allow for variable stiffness, and the semi-conical shaped distal tip to improve tissue fixation.

In still other embodiments, the invention may be directed to one or more methods. For example, a method of creating a medical lead may include coiling a first set of N filar(s) to define a first portion of a medical lead, and coiling a second set of N+M filars to define a second portion of a medical lead having increased stiffness relative to the first portion, wherein N and M are positive integers. The method may further include electrically coupling the first set of N filar(s) to the second set of N+M filars.

In another embodiment, a method may include inserting a J-shaped stylet into a lumen of a medical lead, implanting a semi-conical distal tip of the medical lead into tissue of a patient, and removing the J-shaped stylet from the lumen.

The different embodiments may be capable of providing a number of advantages. For example, the use of a varying number of filars in a lead coil at selected positions along the length of a medical lead can improve stiffness characteristics of medical leads. Moreover, the use of a varying number of filars in a lead coil can achieve improved stiffness with less impact on bending stress on the filars in the lead. In other words, varying the number of filars can be used to increase stiffness without making bending stress to filars of the lead unacceptable for certain applications. Such features may be particularly useful for leads designed to assume a J-shape following implantation, but may be advantageous in numerous other applications as well.

The semi-conical distal tip features can provide advantages in terms of improved tissue fixation to the lead, e.g., by fibrous tissue growth around the tip, and may also be useful in harnessing spring forces to force the lead tip against tissue. Moreover, a semi-conical distal tip may be removable from fibrous tissue with significantly less trauma to a patient than the removal of lead tips that include tines. In some cases, the semi-conical distal tip may be designed such that the conical shape increases in thickness by no more than 25 percent, which may ensure that removal can be made without substantial tissue mutilation. Instead, the tissue may stretch, allowing removal of the lead with reduced trauma relative to lead tips that include tines.

BRIEF DESCRIPTION OF THE DRAWINGS

FIG. 11 is a side view of a distal tip of a medical lead

FIG. 12 is a side view of a distal tip of exemplary medical lead including ridges to improve lead removal.

FIGS. 13 and 14 are cross-sectional front views of distal tips of medical leads including ridges to improve lead removal.

DETAILED DESCRIPTION OF THE INVENTION

The invention is directed to medical leads for use in implantable medical devices. Various features of medical leads are described, many of which may be useful in a variety of different leads used for a variety of different applications. In one embodiment, the invention provides a medical lead of varying stiffness characteristics. In another embodiment, the invention provides a medical lead having a semi-conical shaped distal tip that becomes wider at more distal tip locations. In other words, the distal tip tapers radially outward. The distal tip may be semi-concial in that it takes a form that corresponds to a portion of a cone. These and other embodiments described herein may be used to improve medical leads for a wide variety of applications. Such applications may include specific applications in which a distal end of the lead is implanted in the roof of a patient's right atrium. When implantation in the right atrium is desired, the lead may be formed into a J-shape at a distal end of the lead, e.g., so that the lead tip can be implanted in the roof of the patient's right atrium.

Figure 1:
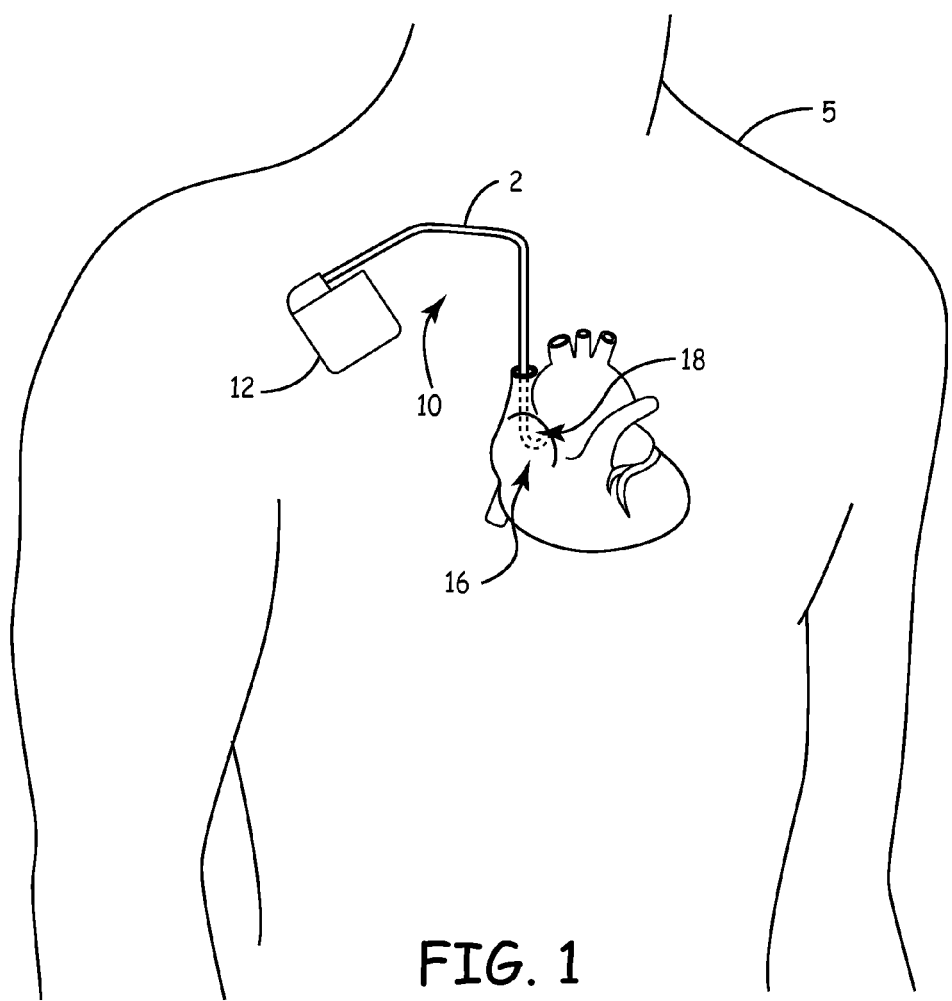
FIG. 1 is a conceptual diagram illustrating an exemplary implantable medical device (IMD) in a human body.

FIG. 1 is a conceptual diagram illustrating an exemplary implantable medical device (IMD) 10 in a human body 5. A similar device may also be used with other living beings. IMD 10 comprises a housing 12 containing various circuitry that controls IMD operations. Housing 12 is typically hermetically sealed to protect the circuitry. Housing 12 may also house an electrochemical cell, e.g., a lithium battery for powering the circuitry, or other elements. The circuitry within housing 12 may be coupled to an antenna to transmit and receive information via wireless telemetry signals.

IMD 10 may comprise any of a wide variety of medical devices that include one or more medical leads and circuitry coupled to the medical leads. By way of example, IMD 10 may take the form of an implantable cardiac pacemaker that provides therapeutic stimulation to the heart. Alternatively, IMD 10 may take the form of an implantable cardioverter, an implantable defibrillator, or an implantable cardiac pacemaker-cardioverter-defibrillator (PCD). IMD 10 may deliver pacing, cardioversion or defibrillation pulses to a patient via electrodes disposed on distal ends of one or more leads 2. In other words, one or more leads 2 may position one or more electrodes with respect to various cardiac locations so that IMD 10 can deliver pulses to the appropriate locations.

The invention, however, is not limited for use in pacemakers, cardioverters of defibrillators. Other uses of the leads described herein may include uses in patient monitoring devices, or devices that integrate monitoring and stimulation features. In those cases, the leads may include sensors disposed on distal ends of the respective lead for sensing patient conditions.

Also, the leads described herein may be used with a neurological device such as a deep-brain stimulation device or a spinal cord stimulation device. In those cases, the leads may be stereotactically probed into the brain to position electrodes for deep brain stimulation, or into the spine for spinal stimulation. In other applications, the leads described herein may provide muscular stimulation therapy, gastric system stimulation, nerve stimulation, lower colon stimulation, drug or beneficial agent dispensing, recording or monitoring, gene therapy, or the like. In short, the leads described herein may find useful applications in a wide variety medical devices that implement leads and circuitry coupled to the leads.

Referring again to FIG. 1, lead 2 assumes a J-shaped configuration. In particular, a distal portion 16 of lead 2 may assume the J-shaped configuration. By way of example, the distal portion 16 which assumes the J-shaped configuration may comprise approximately the distal 80 millimeters of lead 2, although larger or smaller J-shapes could also be used.

In order to achieve a J-shaped distal portion 16, lead 2 may first be implanted into the patient's right atrium. A J-shaped stylet can be straightened and inserted through a lumen of lead 2. Once a distal portion of the stylet is completely inserted into the lumen, the distal portion of the stylet may assume the J-shape and thereby cause the distal portion 16 of lead 2 to likewise assume the J-shape. A distal tip 18 of lead 2, e.g., including an electrode, may then be implanted in the roof of the patient's right atrium, such as between pectinate muscles. As outlined in greater detail below, this distal tip 18 may be formed in a semi-conical shape in which distal tip 18 becomes thicker at more distal locations. The distal tip may be semi-concial in that it takes a form that corresponds to a portion of a cone. Such a semi-conical shape of distal tip 18 may improve fixation within the patient, particularly when distal region 16 of lead 2 assumes the J-shape for implantation in a patient's right atrial roof.

After implanting distal tip 18 in the right atrial roof, the J-shaped stylet can be removed from the inner lumen of lead 2. Following removal of the J-shaped stylet, however, distal region 16 should still retain the J-shape. Various features of lead 2 can help ensure that insertion and removal of the J-shaped stylet can result in distal region 16 of lead 2 remaining in a J-shape. One such feature are filar coils that provide improved stiffness characteristics in distal region 16 to help ensure that lead 2 is flexible enough to assume the J-shape, but stiff enough to maintain the J-shape following removal of the stylet. Another such feature is a semi-conical shaped distal tip that can improve fixation against tissue to help ensure that lead 2 does not lose its J-shape following removal of the stylet.

Lead stiffness is an important concern, particularly when the lead is designed to assume specific forms that facilitate implantation in specific locations within a patient. Again, the J-shaped configuration is only one example where stiffness is an issue. Many other desired forms of a lead may also benefit from the stiffness features described herein.

Conventionally, increased stiffness, e.g., in a distal portion of a lead, was achieved by increasing the pitch of a coiled filar that electrically couples the electrode on the distal tip of the lead to a proximal end of the lead. In particular, the filar could be coiled with a relatively small pitch to ensure flexibility in a major portion of the lead body. The term "pitch" refers to the longitudinal distance between a first location of a filar and a second location of the same filar after one coiled revolution about a lumen of the medical lead. Near the distal portion of the lead, the pitch of the filar can be increased, which may increase the stiffness.

An increase in pitch of a filar, however, has several drawbacks particularly in relation to filar stress when the lead is bent to a given radius. For example, when the pitch of the filar increases, stress to the filar upon bending of the lead drastically increases. More specifically, bending of the lead in locations of increased filar pitch could cause damage to the filar because the filar itself may physically bend. For coils typically designed for this application, the coiled filar stress it approximately proportional to the coil pitch for a given bend radius. It is highly desirable to design a lead that can achieve increased stiffness in one or more locations along a lead body, without causing drastic stress increases to the filar(s) when the lead is bent.

In order to achieve improved lead stiffness without major adverse impacts on mechanical filar stress, the invention may introduce variable numbers of filars at different locations along a lead body. More specifically, a medical lead 2 may comprise a first coiled portion including N filar(s), and a second coiled portion electrically coupled to the first coiled portion. The second coiled portion may include N+M filars to produce increased stiffness in the second coiled portion relative to the first coiled portion, wherein N and M are positive integers. The increased number of filars can improve stiffness of the lead at a desired location, such as in distal region 16 of lead 2. The introduction of additional filars can avoid drastic pitch increases in the coils, however, ensuring that filar stress is more manageable. The number of filars and the pitch of the filars in any given region of the lead may collectively define the lead stiffness in that region. Accordingly, these variables can be used to define a desired stiffness for various medical lead applications.

Other variables that can affect lead stress include the diameters of the filars and the diameters of the coils. Larger diameter filars generally increases the lead stiffness and larger diameter coils of the respective filar generally decreases lead stiffness. These variables may also be defined so as to achieve a desired lead stiffness.

Figure 2:
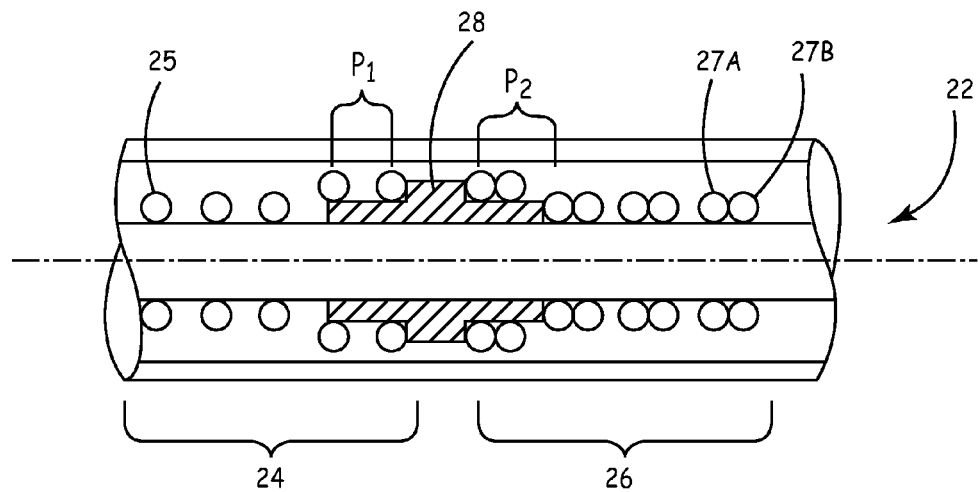
FIG. 2 is a cross-sectional side view of an implantable medical lead according to an embodiment of the invention.
Figure 3:
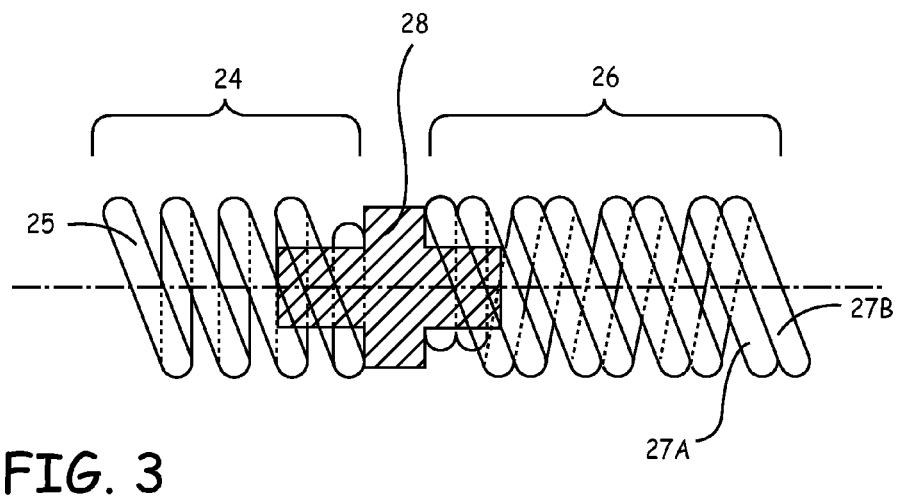
FIG. 3 is a top view of a coil structure within the medical lead illustrated in FIG. 2.

FIG. 2 is a cross-sectional side view of a medical lead according to an embodiment of the invention. FIG. 3 is a top view of a coil structure in the medical lead illustrated in FIG. 2. Medical lead 22 comprises a first coiled portion 24 including one coiled filar 25 extending along a first segment of lead 22, and a second coiled portion 26 including two coiled filars 27A, 27B extending along a second segment of lead 22. An electrically conductive bus 28 electrically couples filar 25 to filars 27A and 27B. In particular, electrically conductive bus 28 may be an interconnect structure that provides both electrical and mechanical coupling of first and second portions. In first portion 24, the single filar 25 defines an electrically conductive path, and in second portion 26, the two filars 27A, 27B define the electrically conductive path. The introduction of additional filars in second portion 26 causes the stiffness of second portion 26 to be larger than that of first portion 24. Still, the stress in second portion 26, e.g., in response to bending, may be substantially reduced relative to conventional leads that achieve increased stiffness by increasing filar pitch rather than using an increased number of filars as described herein.

The pitch refers to the longitudinal distance between a first location of a filar and a second location of the same filar after one coiled revolution about the lumen. As illustrated in FIG. 2, the pitch $P_1$ in first portion 24 is slightly smaller than the pitch $P_2$ in second portion. The invention, however, is not limited in that respect, and in other configurations, the pitch $P_2$ can be made the same as or smaller than the pitch $P_1$. In short, the introduction of additional filars can define increased stiffness without regard to changes in pitch. Changes in pitch, however, can also affect stiffness. Thus, in accordance with the invention, both the number of filars in any given portion of a lead, and the pitch of the filars in the given portion of the lead can collectively define stiffness of the lead in the given portion of the lead.

Figure 4:
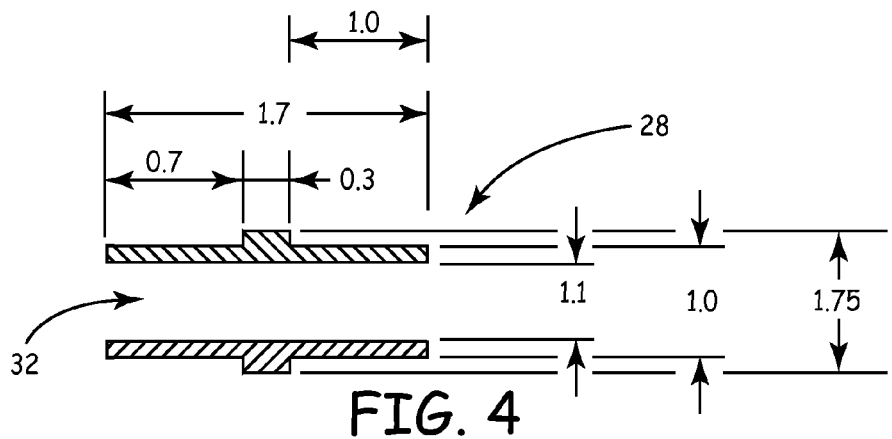
FIG. 4 is a cross-sectional side view of an exemplary electrically conductive bus that may be used in a medical lead to couple N filar(s) to N+M filars.

FIG. 4 is a cross-sectional side view of an exemplary electrically conductive bus 28 that may be used in a medical lead to couple N filar(s) to N+M filars. Electrically conductive bus 28 generally comprises an electrically conductive material for coupling N filar(s) to N+M filars. For example, electrically conductive bus 28 may be a cylindrical shaped structure with a through-hole 32 which forms part of a lumen of the lead. The diameter of through hole 32 may be sized to permit a stylet to pass. Electrically conductive bus 28 may define a first region 33 for electrically coupling to the N filar(s), and a second region 34 for electrically coupling to the N+M filars. Preferably, electrically conductive bus 28 is formed of a biocompatible metal. Exemplary dimensions (in millimeters) of electrically conductive bus 28 are illustrated in FIG. 4, although a wide variety of different shapes and sizes may also be used to achieve a bus in accordance with the invention.

Figure 5:
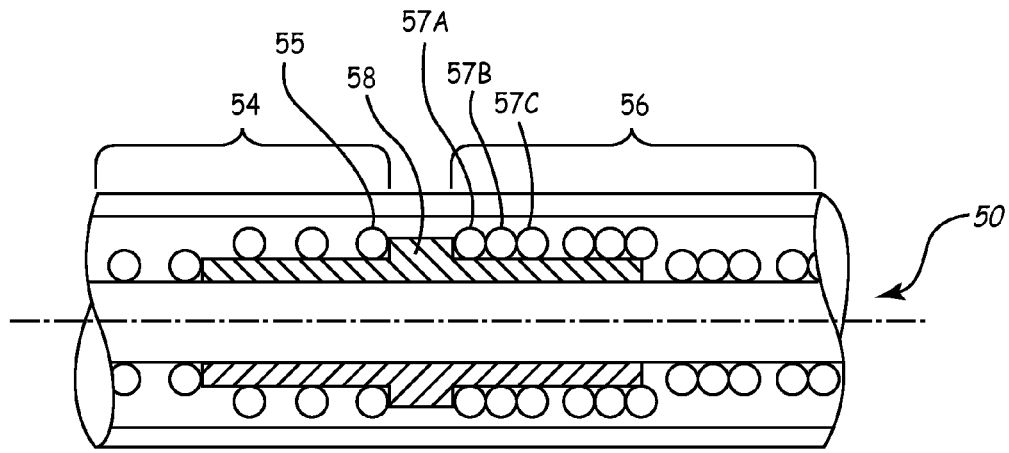
FIGS. 5-7 are cross-sectional side views of medical leads according to embodiments of the invention.

FIG. 5 is another cross-sectional side view of a medical lead 50 according to an embodiment of the invention. In that case, first portion coiled portion 54 includes one coiled filar 55, and second coiled portion 56 includes three coiled filars 57A, 57B, 57C. Electrically conductive bus 58 electrically couples filar 55 to filars 57A-57C. In first portion 54, filar 55 defines an electrically conductive path, and in second portion 56, the three filars 57A, 57B, 57C define the electrically conductive path. The introduction of a number of additional filars in second portion 56 causes the stiffness of second portion to be larger than that of first portion 54. However, the stress in second portion 56, e.g., in response to bending, may be substantially reduced relative to conventional lead stiffness features that use increased pitch rather than an increased number of filars to achieve increased lead stiffness.

Figure 6:
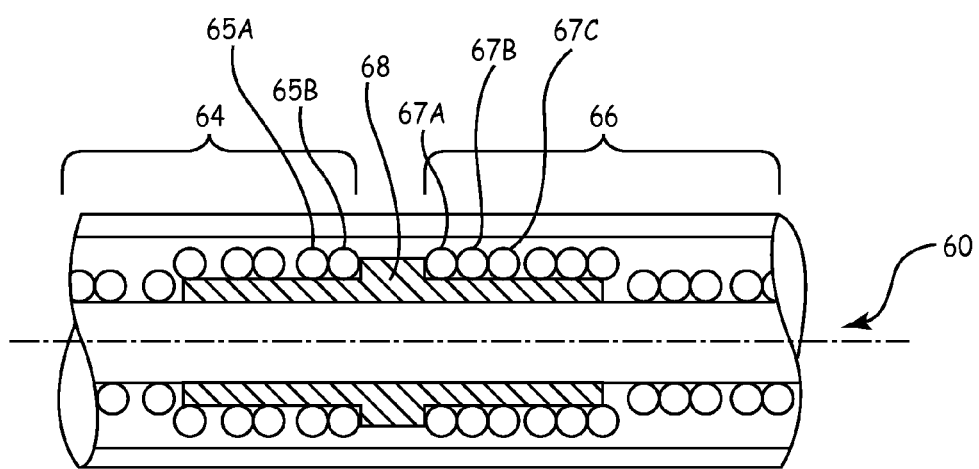

FIG. 6 is another cross-sectional side view of a medical lead 60 according to an embodiment of the invention. In lead 60, first portion coiled portion 64 includes two coiled filars 65A, 65B, and second coiled portion 66 includes three coiled filars 67A, 67B, 67C. Electrically conductive bus 68 electrically couples filars 65A and 65B to filars 67A-67C.

Figure 7:
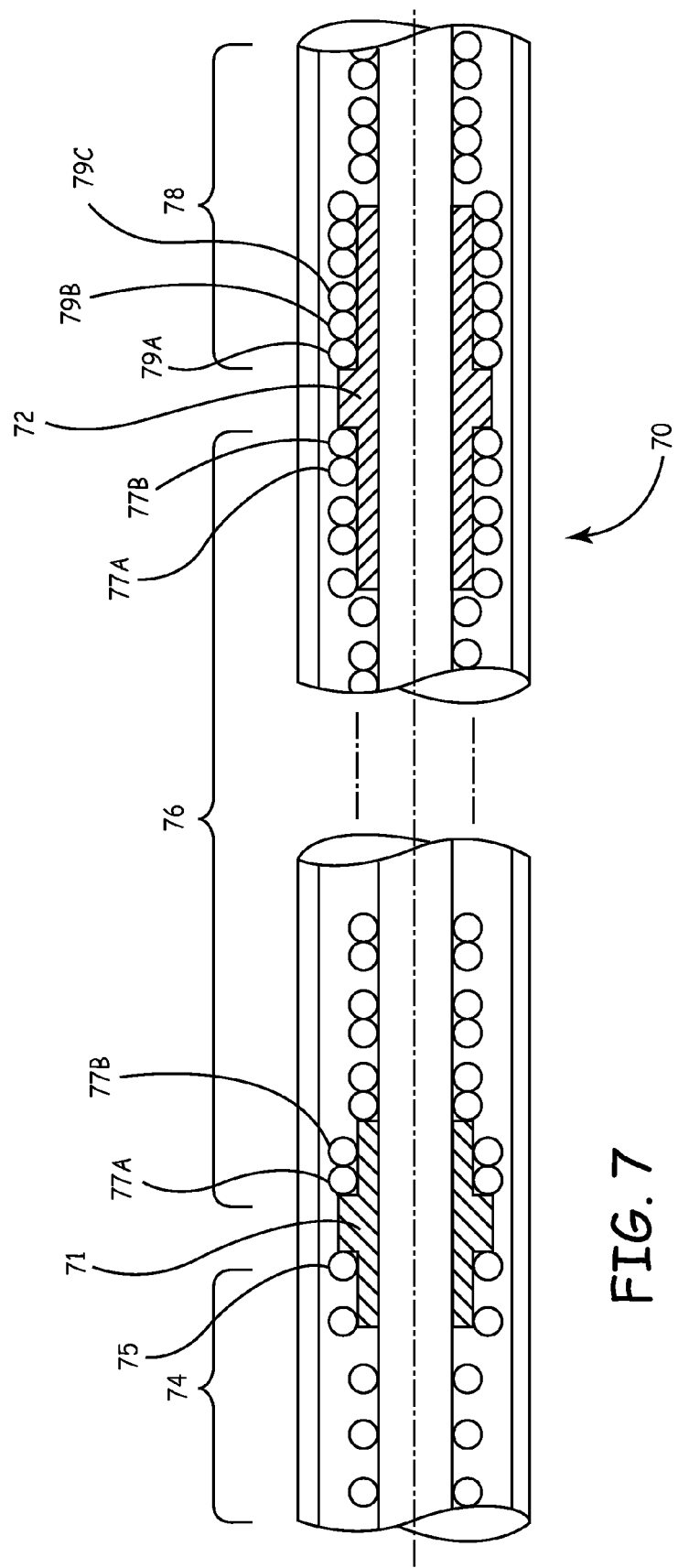

FIG. 7 is another cross-sectional side view of a medical lead 70 according to an embodiment of the invention. As shown in FIG. 7, medical lead 70 defines at least three coiled portions. A first portion coiled portion 74 includes one coiled filar 75, and second coiled portion 76 includes two coiled filars 77A and 77B. Furthermore, a third coiled portion 78 includes three coiled filars 79A, 797B, 79C. Electrically conductive bus 71 electrically couples filar 75 to filars 77A and 77B, and electrically conductive bus 72 electrically couples filars 77A and 77B to filars 79A-79C.

Numerous other combinations of filars could also be used in accordance with the invention In general, the invention provides a medical lead comprising a first coiled portion including N filar(s) extending along a first segment of the lead, and a second coiled portion electrically coupled to the first coiled portion. The second coiled portion may include N+M filars extending along a second segment of the lead to define increased stiffness of the second coiled portion relative to the first coiled portion, wherein N and M are positive integers. In some cases, the portion defining increased stiffness may correspond to a distal end of the lead, and in other cases, the portion defining increased stiffness may correspond to a proximal end of the lead. In still other cases, the portion defining increased stiffness may correspond to a portion between the proximal and distal ends.

Also, varying levels of stiffness may be defined at any desired lead location in accordance with the invention. For example, a first portion may include N filar(s), a second portion may include N+M filars, a third portion may include N+M+O filars, a fourth portion may include N+M+O+P filars, and so forth. N, M, O and P may represent positive integers. Alternatively a first portion may include N filar(s), a second portion may include N+M filars, a third portion may include N+M−O filars. Put another way, a lead may include N+M+O filars, where N and M are positive integers, and O is a positive or negative integer. Also, a lead may include N+M+O+P filars, where N and M are positive integers, and O and P are positive or negative integers. A wide variety of configurations of a lead may be defined in this manner in order to achieve desired stiffness for a given medical lead application.

As described above with reference to FIGS. 2-7, an electrically conductive bus can be used to electrically couple the N filar(s) of one portion of a medical lead to the N+M filars of another portion of a medical lead. To create such a lead, the filars can be wound around an inner core, and then the inner core can be removed. More specifically, a cylindrical shaped electrically conductive bus may be inserted over an inner core, and N filar(s) can be wound around the inner core to define a first portion of a lead. The N filar(s) can be electrically coupled to the electrically conductive bus on one side of the bus, and may be welded, soldered, crimped or otherwise affixed to the bus to ensure electrical contact. N+M filars can then be wound around the inner core to define a second portion of the lead. The N+M filars can be electrically coupled to the electrically conductive bus on the other side of the bus, i.e., the side opposite the electrical contact to the N filar(s). The inner core can then be removed to define a lead having a first coiled portion with N filar(s) and a second coiled portion with N+M filars. The location of the inner core can define a common lumen that extends through the first coiled portion and the second coiled portion of the lead following removal of the inner core.

Figure 8:
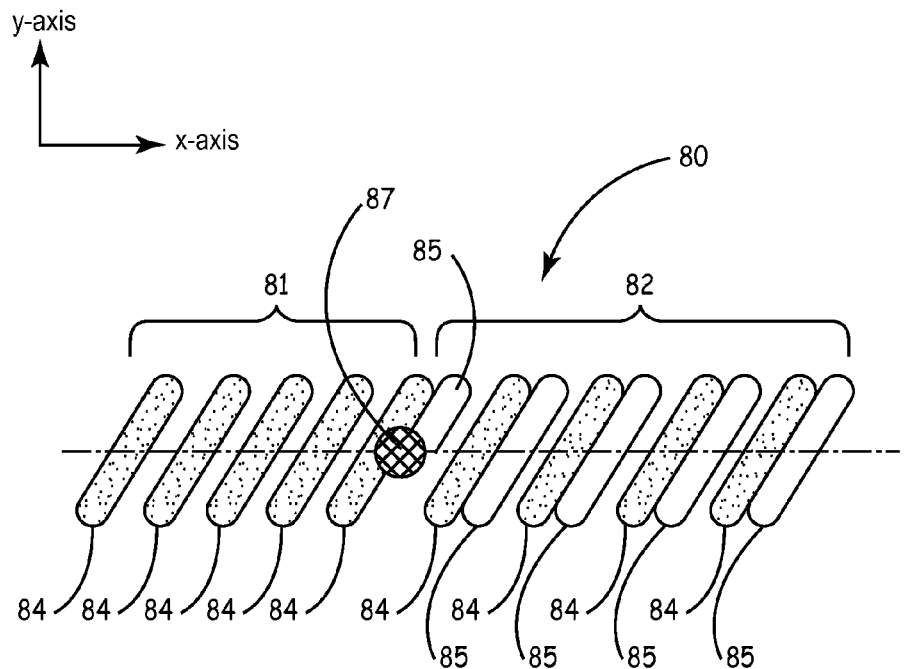
FIG. 8 is a top view of an embodiment of first and second coiled portions of a medical lead in which one filar is welded to another filar at the juncture of the first and second coiled portions.

FIG. 8 is a top view of an embodiment of first and second coiled portions 81, 82 of a medical lead 80 in which one filar 84 is welded to another filar 85 at the juncture of the first coiled portion 81 and the second coiled portion 82. In particular, a weld 87 may be applied to electrically couple filar 84 to filar 85. In this manner, first and second coiled portions 81, 82 of a medical lead 80 can be defined in which first coiled portion 81 includes N filar(s) and second coiled portion 82 included N+M filars. The N+M filars of second coiled portion 82 carry a common electrical potential, and are electrically coupled to the N filar(s) of first coiled portion 81.

Figure 8A:
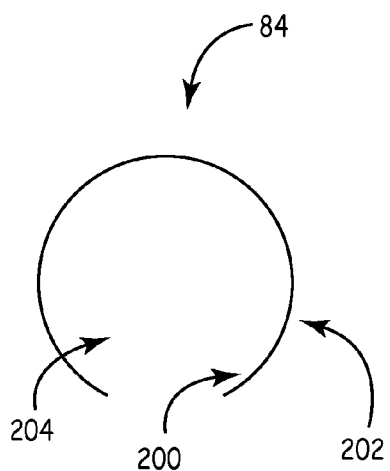
FIG. 8A is a top view of a N filar.
Figure 8B:
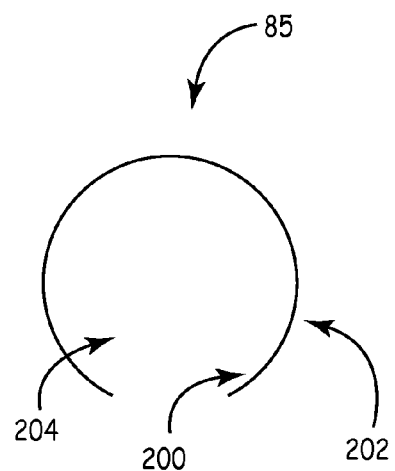
FIG. 8B is a top view of a M filar.

In order to create a medical lead as illustrated in FIG. 8, filar 84 may be coiled around an inner core. Filar 85 may then be coiled around a portion of the inner core. Filar 85 can then be welded to filar 84 to define medical lead 80 that includes first coiled portion 81 and second coiled portion 82. The inner core can then be removed to define a lumen inside the coiled portions 81, 82. In first portion 81, the single filar 84 defines an electrically conductive path, and in second portion 82, the two filars 84 and 85 define the electrically conductive path. Filars 84 and 85 are integrally wound or intertwined. Specifically, filar 84 is directly adjacent to filar 85 along the same X-axis (also referred to as the first axis). Moreover, filar 84 and filar 85 possess a consistent or the same height along the y-axis (also referred to as the second axis). Additionally, each filar 84, 85 generally form an opening 204, as depicted in FIG. 8A and FIG. 8B. Filar 84 and 85 each possess a first side 200 and a second side 202. First side 200 is generally the inner surface whereas second side 202 is generally the outer surface of filars 84, 85. Opening 204 is formed by first side 200 of filars 84, 85. Skilled artisans appreciate that filars 84 and 85 are adjacent to one another. Additionally, filars 84 and 85 possess openings 204 that are adjacent to one another.

Alternatively, filars 84 and 85 may be coiled together around an inner core. Filar 85 may then be cut, i.e., removed from first portion 81. After cutting filar 85, filar 85 may be welded to filar 84 via weld 87. The inner core can then be removed to define a lumen of lead 80.

The lead configuration illustrated in FIG. 8 may also define any number of filars. In general, first portion 81 may include N filar(s) and second portion 82 may include N+M filars, where N and M are positive integers. In the configuration of FIG. 8, the N filar(s) of first portion 81 are the same filars as the N filar(s) of second portion 82. The M filar(s) of second portion 82 do not form part of first portion 81.

The use of varying number of filars can also apply to bipolar leads or other types of multi-coil leads. A bipolar lead includes an inner coil and an outer coil. The inner coil is used to define an electrical path for a first electrode, e.g., a ground electrode, and the outer coil is used to define a second electrode, e.g., a stimulation electrode. Insulating tubing may be added around one or both coils. Varying number of filars may be used in a bipolar lead with respect to either the inner coil, the outer coil, or both to define desired stiffness characteristics.

Figure 9:
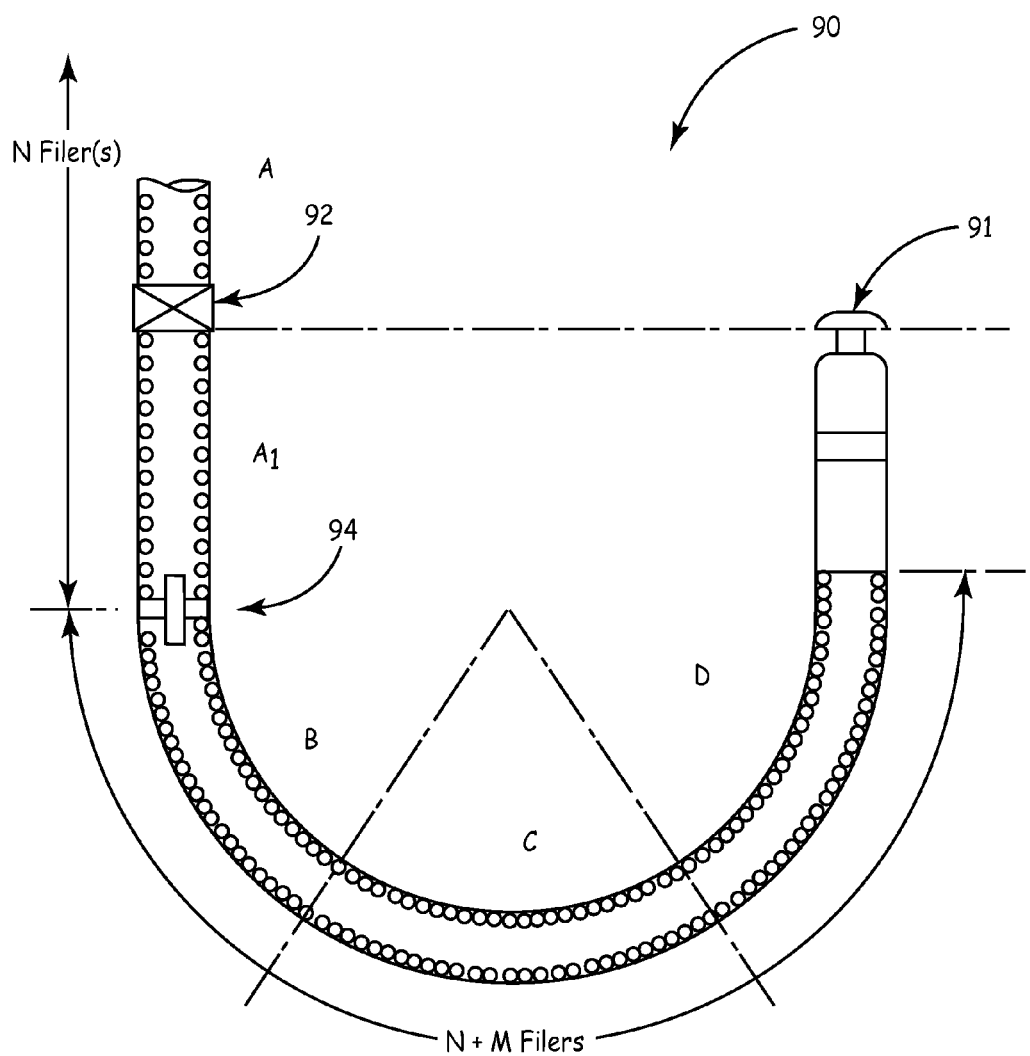
FIG. 9 is an exemplary cross sectional side view of a distal end of a medical lead assuming a J-shaped configuration.

FIG. 9 is a cross-sectional side view of a distal region of lead 90 formed into a J-shape. Lead 90 may include an electrode 91 on a distal tip. A radio-opaque or echogenic ring 92 may be added as a reference point for a physician so that a desired J-shape can be achieved. Accordingly, the location of ring 92 on lead 90 may be defined so that a J-shape of desired shape and radius can be more easily achieved by a physician. Lead 90 may define two or more different regions (labeled A, $A_1$, B, C and D). The different regions of lead 90 may define different stiffness to help ensure that the J-shape can be maintained following removal of a J-shaped stylet from an inner lumen of lead 90. An electrically conductive bus 94 can be used so that N filar(s) of regions A and $A_1$ can be electrically coupled to N+M filars of regions B, C and D. Other variables of respective regions A, $A_1$, B, C and D may also be selected to promote desired stiffness characteristics, including pitch, filar diameter, and the diameter of the coil(s).

TABLE 1, provided below, includes empirical evidence of characteristics of a lead similar to that illustrated in FIG. 9. The different regions and number of filars per region are identified in the first column of TABLE 1. An electrically conductive bus was implemented to connect the two filars of region $A_1$ to the three filars of region B. For each region, the pitch, stress and bending stiffness are listed. The measured quantities were obtained from a bipolar lead in which the inner coil was substantially unchanged of the whole lead body. The outer coil included the measured variables of differing pitch and number of filars per coiled region.

TABLE 1

|  | A<br>2-FILAR | $A_1$<br>2-FILAR | B<br>3-FILAR | C<br>3-FILAR | D<br>3-FILAR |
|---|---|---|---|---|---|
| PITCH (mm) | 0.57 | 0.57 | 0.78 | 0.9 | 1.15 |
| STRESS ($N/mm^2$) | 459 | 459 | 500 | 700 | 850 |
| BEND STIFFNESS ($N*mm^2$/radian) | 14.2 | 14.2 | 19.5 | 23.0 | 29.5 |

TABLE 2 provides a reference for the data in TABLE 1. The measured quantities of TABLE 2 were obtained from a bipolar lead in which the inner coil was substantially unchanged of the whole lead body. The outer coil included the measured variables of differing pitch, but the number of filars did not change in TABLE 2. The regions listed in TABLE 2 also correspond to the regions of lead 90 illustrated in FIG. 9, but the number of filars per region in TABLE 2 was held constant.

TABLE 2

|  | $A_1$/A<br>2-FILAR | B<br>2-FILAR | C<br>2-FILAR | D<br>2-FILAR |
|---|---|---|---|---|
| PITCH (mm) | 0.57 | 0.95 | 1.30 | 1.65 |
| STRESS ($N/mm^2$) | 459 | 712 | 988 | 1282 |
| BEND STIFFNESS ($N*mm^2$/radian) | 14.2 | 18.9 | 23.4 | 30.1 |

Comparison of the data in TABLE 1 to that of TABLE 2 illustrates the advantages that can be achieved by introduction of more filars to increase stiffness. In particular, the data in TABLE 2 relative to that of TABLE 1 illustrates that approximately the same bending stiffness can be achieved with great reductions in stress when additional filars are introduced. In particular, the data in TABLE 1 relative to TABLE 2 achieved a 33% stress reduction.

TABLES 3 and 4 illustrate similar results. Again the data in TABLES 3 and 4 can be read with respect to J-shaped distal regions of a leads similar to lead 90 of FIG. 9. The measured quantities of TABLES 3 and 4 were obtained from bipolar leads in which the inner coil was substantially unchanged of the whole lead body. The outer coil included the measured variables of differing pitch. The number of filars did not change in TABLE 3, but did change in TABLE 4. With respect to TABLE 4, an electrically conductive bus was implemented to connect the filar of region $A_1$ to the two filars of region B. The filars of the different leads quantified in TABLES 1-4 had 0.25 millimeter diameters, and the coiled diameters were approximately 1.60 millimeters in every respective region. In other words, the filar diameter and coiled diameter did not change in the different leads quantified in TABLES 1-4.

TABLE 3

|  | A<br>1-FILAR | $A_1$<br>1-FILAR | B<br>1-FILAR | C<br>1-FILAR | D<br>1-FILAR |
|---|---|---|---|---|---|
| PITCH (mm) | 0.57 | 0.57 | 0.90 | 1.30 | 1.70 |
| STRESS ($N/mm^2$) | 473 | 473 | 767 | 1035 | 1320 |
| BEND STIFFNESS ($N/mm^2$/radian) | 14.0 | 14.0 | 19.24 | 24.07 | 30.2 |
| COIL DIAMETER (mm) | 1.6 | 1.6 | 1.6 | 1.6 | 1.6 |

TABLE 4

|  | A<br>1-FILAR | $A_1$<br>1-FILAR | B<br>2-FILAR | C<br>2-FILAR | D<br>2-FILAR |
|---|---|---|---|---|---|
| PITCH (mm) | 0.50 | 0.50 | 0.63 | 1.0 | 1.38 |
| STRESS ($N/mm^2$) | 406 | 406 | 509 | 800 | 1090 |
| BEND STIFFNESS ($N/mm^2$/radian) | 9.65 | 9.65 | 15.3 | 20.65 | 26.0 |
| COIL DIAMETER (mm) | 1.6 | 1.6 | 1.6 | 1.6 | 1.6 |

Comparison of the data in TABLE 3 to that of TABLE 4 further illustrates the advantages that can be achieved by introduction of more filars to increase stiffness. In particular, the data in TABLE 4 relative to that of TABLE 3 illustrates that approximately the same bending stiffness can be achieved with great reductions in stress when additional filars are introduced.

Figure 10:
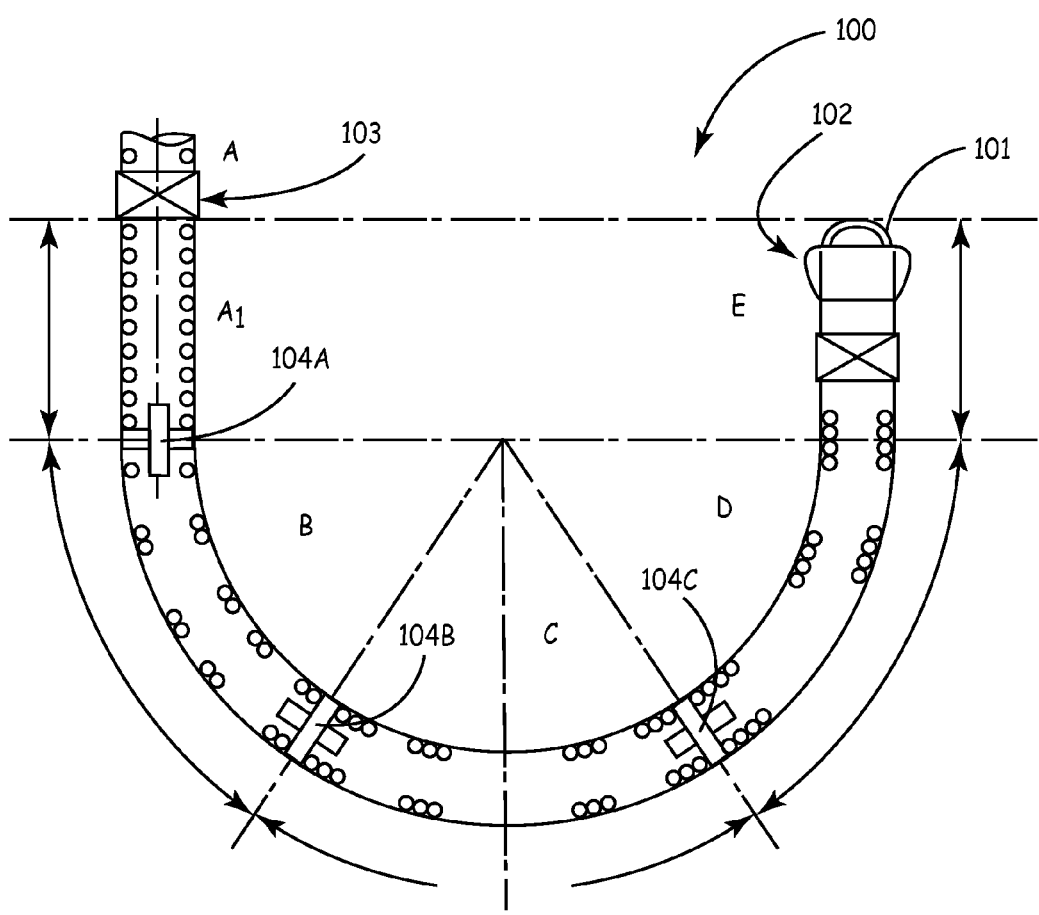
FIG. 10 is another exemplary cross sectional side view of a distal end of a medical lead assuming a J-shaped configuration.

FIG. 10 is another cross-sectional side view of a distal region of lead 100 formed into a J-shape. Lead 100 may include an electrode 101 on a distal tip 102. Moreover, distal tip 102 may define a semi-conical shape in which distal tip 102 becomes thicker at more distal locations. In other words, distal tip 102 tapers radially outward. Additional details of the advantages of a semi-conical shaped distal tip are provided below with reference to FIGS. 11-15.

A radio-opaque or echogenic detectable ring 103 may be added as a reference point for a physician so that a desired J-shape can be achieve. Accordingly, the location of ring 103 on lead 100 may be defined so that a J-shape of desired shape and radius can be more easily achieved by a physician. Lead 100 may define a number of different regions (labeled A, $A_1$, B, C, D and E). The different regions of lead 90 may define different stiffness to help ensure that the J-shape can be maintained following removal of a J-shaped stylet from an inner lumen of lead 100. One or more electrically conductive buses 104A-104C can be used so a number of filars of a respective regions can be electrically coupled to a different number of filars of a different region. Other variables of respective regions A, $A_1$, B, C and D may also be selected to promote desired stiffness characteristics. These other variables include pitch, filar diameter, and the diameter of the coil(s).

TABLES 5-7 below include additional empirical evidence of characteristics of a lead similar to that illustrated in FIG. 10. The different regions and number of filars per region are identified in the first column of each of TABLES 5-7. For each region, the pitch, stress, bending stiffness and filar diameter are listed. Electrically conductive buses were implemented to connect the filars of adjacent regions in which the number of filars changed. The measured quantities were obtained from a bipolar lead in which the inner coil was substantially unchanged of the whole lead body. The outer coil included the measured variables of differing pitch and number of filars per coiled region. The coil diameter of the outer coil of the respective leads quantified in TABLES 5-7 was approximately 1.6 millimeters in every region.

TABLE 5

| | 1-FILAR | 2-FILAR | 2-FILAR | 3-FILAR |
| --- | --- | --- | --- | --- |
| PITCH (mm) | 0.50 | 0.65 | 1.0 | 0.9 |
| STRESS (N/mm²) | 406 | 525 | 796 | 722 |
| BEND STIFFNESS (N/mm²/radian) | 9.64 | 15.6 | 20.6 | 25.9 |
| FILAR DIAMETER (mm) | 0.25 | 0.25 | 0.25 | 0.25 |

TABLE 6

| | 1-FILAR | 2-FILAR | 3-FILAR | 3-FILAR |
| --- | --- | --- | --- | --- |
| (mm)H mm | 0.50 | 0.65 | 0.86 | 0.9 |
| STRESS (N/mm²) | 406 | 525 | 693 | 722 |
| BEND STIFFNESS (N/mm²/radian) | 9.64 | 15.6 | 25.07 | 25.9 |
| FILAR DIAMETER (mm) | 0.25 | 0.25 | 0.25 | 0.25 |

TABLE 6

| | 1-FILAR | 2-FILAR | 3-FILAR | 4-FILAR |
| --- | --- | --- | --- | --- |
| PITCH (mm) | 0.50 | 0.65 | 0.86 | 1.20 |
| STRESS (N/mm²) | 406 | 525 | 693 | 953 |
| BEND STIFFNESS (N/mm²/radian) | 9.64 | 15.6 | 25.1 | 41.1 |
| FILAR DIAMETER (mm) | 0.25 | 0.25 | 0.25 | 0.25 |

The data in TABLES 5-7 further illustrate the advantages that can be achieved by introduction of more filars to increase stiffness. In particular, the use of additional filars to increase stiffness can achieve higher quantities of stiffness, and also reduced quantities of bending stress. This is highly advantageous, particularly for medical leads designed to assume shapes that facilitate implantation in hard to reach locations. The J-shaped lead is only one example.

Other variables that can affect lead stiffness include the diameter of the filars and the diameter of the coils. Larger diameter filars generally increases stiffness and larger diameter coils of the respective filar generally decreases stiffness. These variables may also be defined so as to achieve a desired lead stiffness. For example, if a first portion defines N filar(s) and a second portion defines N+M filars, one or more of the N+M filars of the second portion may have different diameters than the N filar(s) of the first portion in order to define a desired stiffness.

Also, the second portion may define a different coiled diameter than the first portion, which could be accommodated by an electrically conductive bus that tapers to change diameter at one end relative to the other end of the bus. In short, variables including the number of filars, the pitch of the filars, the diameter of the filars, and the diameter of the coils may be selected to promote a desired stiffness and filar stress of a medical lead, and may change for different portions or regions of the lead in accordance with the invention.

FIG. 11 is a side view of a distal tip 111 of a medical lead 110. In particular, a semi-conical shaped tip 111 is formed on a distal end of lead 110. The semi-conical shaped tip 111 becomes wider at more distal locations, i.e., tip 111 becomes larger at locations further from a proximal end of lead 110. In other words, the distal tip 111 tapers radially outward. An electrode 115 or other element such as a sensor may be located on distal tip 111. The tip is referred to as semi-conical because it takes a form that corresponds to a portion of a cone.

A semi-conical distal tip 111 may find uses in a variety of lead applications, including specific applications in which lead 110 assumes a J-shaped distal region for implantation in a patient's right atrium. The semi-conical shaped tip 111 may provide a structure that allows fibrous tissue growth to anchor lead 110, but may be less aggressive than conventional tines, allowing removal without substantial tissue mutilation. In other words, semi-conical distal tip 111 can be removed from fibrous tissue with significantly less trauma to a patient than the removal of lead tips that include tines.

Semi-conical distal tip 111 may be designed such that the conical shape increases in thickness by no more than 25 percent. In other words, a radius $R_2$ may be less than approximately 125 percent of the radius $R_1$. Angle ($\alpha$) as well as length (L) may be defined to ensure that radius $R_2$ is larger than radius $R_1$ by between approximately 10 and 25 percent. Such sizes of radii $R_1$ and $R_2$ may ensure that removal can be made without substantial tissue mutilation. Instead, the tissue may stretch, allowing removal of the lead with reduced trauma relative to lead tips that include tines. Tissue stretching beyond 25 percent is very unlikely, so the upper bound of radius $R_2$ being no greater than 25 percent larger than $R_1$ can help ensure that tissue stretching can accommodate removal of lead 110. Larger variations between $R_1$ and $R_2$, however may be useful as well.

FIG. 12 is a side view of a distal tip 121 of exemplary medical lead 122 including ridges 123 to improve lead removal. The outer FIGS. 13 and 14 are cross-sectional front views of distal tips 121A, 121B of medical leads including ridges 123A-123C (FIG. 13) and 123D-123G (FIG. 14) to improve lead removal. Medical lead 120 defines a semi-conical shaped tip 121 formed on a distal end of lead 120, which can provide the same advantages mentioned above in relation to FIG. 11. In addition, one or more ridges 123 can further improve lead removal from tissue. Such improved lead removal can reduce patient trauma. An outer radius of the ridges may be less than $R_2$ which can ensure that the ridges do not cause excessive tissue stretching upon removal of the lead. Also the distance d may be less than half of length L.

Figure 15:
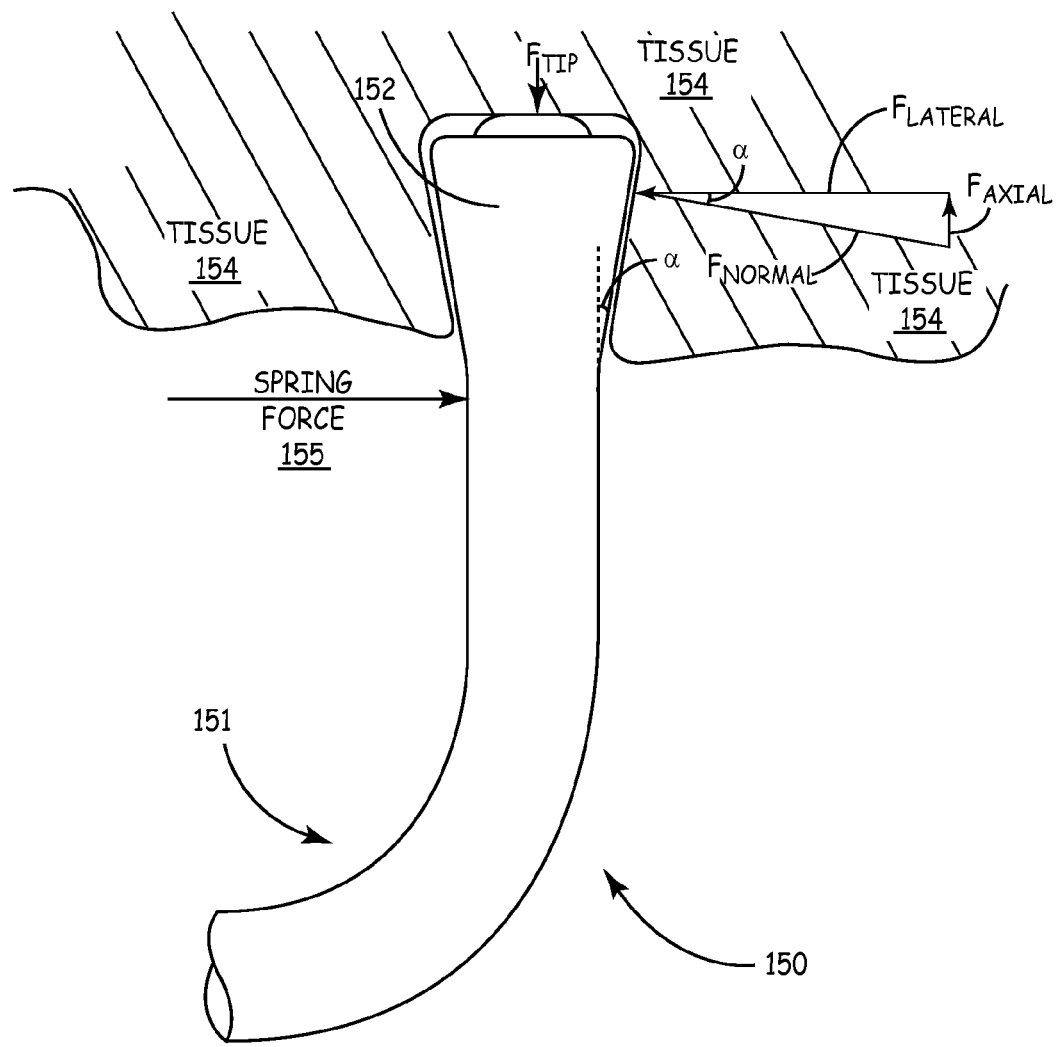
FIG. 15 is a side view of a J-shaped distal tip of a medical lead implanted against tissue of a patient.

FIG. 15 is a side view of a J-shaped distal region 151 of a medical lead 150 implanted against tissue 154 of a patient. Tissue 154, for example, may correspond to pectinate muscles of a patients right atrial roof. Thus, distal tip 152 may be implanted between two pectinate muscles. Lead 150 is substantially similar to lead 110 of FIG. 11 in that distal tip 152 defines a semi-conical shape that becomes larger at more distal regions. If desired, lead 150 may optionally include ridges as illustrated in FIGS. 12-14.

FIG. 15 illustrates an additional advantage that can be achieved with a semi-conical shaped distal tip 152 when used in a medical lead 150 that defines a J-shaped distal region 151. As mentioned above, in order to create the J-shaped distal region 151, a J-shaped stylet can be straightened and inserted through a lumen of medical lead 150. Once a distal portion of the stylet is completely inserted into the lumen, the distal portion of the stylet my assume the J-shape and thereby cause the distal region 151 of medical lead 150 to likewise assume the J-shape. Distal tip 152 can then be implanted in tissue 155, which may correspond to the roof of the patient's right atrium. The stylet can then be removed from the inner lumen of the medical lead.

Following removal of the stylet, the medical lead 150 may have a natural tendency to assume its original shape. In other words, the distal region 151 may define a spring force 155 following removal of the stylet. Spring force 155 tends to force distal region 151 out of the J-shape and into its original shape.

Semi-conical shaped distal tip 152 can harness spring force 155 to improve anchoring in tissue 154. In particular, if distal tip 152 is semi-conical shaped having a larger radius at more distal locations, the normal force ($F_{NORMAL}$) that counter balances spring force 155 will include an axial component ($F_{AXIAL}$) and a lateral component ($F_{LATERAL}$). In a static (non-moving) situation, $$F_{LATERAL} = -(\text{spring force 155}), \text{ and}$$

$$\tan(\alpha) = F_{AXIAL}/F_{LATERAL},$$

$$F_{AXIAL} = -F_{TIP}$$

$$F_{AXIAL} = \tan(\alpha) * F_{LATERAL}, \text{ and}$$

$$F_{AXIAL} = -\tan(\alpha) * (\text{spring force 155})$$

Importantly, semi-conical shaped distal tip 152 can harness spring force 155 to improve anchoring in tissue 154. The angle ($\alpha$) can be selected to define $F_{AXIAL}$ so that enough anchoring force is achieved for any given use of medical lead 150. $\alpha$ may correspond to one-half of a cone angle of the semi-conical tip. The semi-conical shaped distal tip 152 acts similar to a wedge when spring force 155 is present. Accordingly, semi-conical shaped distal tip 152 can be wedged into tissue 154 in response to spring force 154 to improve anchoring of tip 152 in tissue 154.

A number of embodiments of the invention have been described. However, one skilled in the art will appreciate that the invention can be practiced with embodiments other than those disclosed. The disclosed embodiments are presented for purposes of illustration and not limitation, and the invention is limited only by the claims that follow.

What is claimed is:

1. A medical lead comprising:
   a first coiled portion including N filar(s) extending along a first segment of the lead; and
   a second coiled portion electrically coupled to the first coiled portion, the second coiled portion including N+M filars extending along a second segment of the lead, the N+M filars producing increased stiffness of the second coiled portion relative to the first coiled portion, wherein N and M are positive integers, the second coiled portion being located at a more distal end of the medical lead relative to the first coiled portion;
   wherein the M filar(s) in the second coiled portion form M filar coils in the second coiled portion;
   wherein the N filar(s) in the second coiled portion form N filar coils in the second coiled portion;
   wherein at least one M filar coil in the second coiled portion has a coil diameter that is the same as a coil diameter of at least one of the N filar coils;
   an electrode located on a distal tip of the medical lead, the electrode being electrically coupled to the second coiled portion; and
   an electrically conductive bus to electrically couple the N filar(s) of the first coiled portion to the N+M filars of the second coiled portion.

2. A medical lead comprising:
   a first coiled portion including N filar(s) extending along a first segment of the lead; and
   a second coiled portion electrically coupled to the first coiled portion, the second coiled portion including N+M filars extending along a second segment of the lead, the N+M filars producing increased stiffness of the second coiled portion relative to the first coiled portion, wherein N and M are positive integers, the second coiled portion being located at a more distal end of the medical lead relative to the first coiled portion;
   wherein the M filar(s) in the second coiled portion form M filar coils in the second coiled portion;
   wherein the N filar(s) in the second coiled portion form N filar coils in the second coiled portion;
   wherein at least one M filar coil in the second coiled portion has a coil diameter that is the same as a coil diameter of at least one of the N filar coils;
   an electrode located on a distal tip of the medical lead, the electrode being electrically coupled to the second coiled portion; and a weld to electrically couple the M filar(s) of the second coiled portion to the N filar(s) of the first coiled portion, the N filar(s) of the first coiled portion being the same as the N filar(s) of the second coiled portion.

3. A medical lead comprising:
a first coiled portion including N filar(s) extending along a first segment of the lead; and
a second coiled portion electrically coupled to the first coiled portion, the second coiled portion including N+M filars extending along a second segment of the lead, the N+M filars producing increased stiffness of the second coiled portion relative to the first coiled portion, wherein N and M are positive integers, the second coiled portion being located at a more distal end of the medical lead relative to the first coiled portion;
wherein the M filar(s) in the second coiled portion form M filar coils in the second coiled portion;
wherein the N filar(s) in the second coiled portion form N filar coils in the second coiled portion;
wherein at least one M filar coil in the second coiled portion has a coil diameter that is the same as a coil diameter of at least one of the N filar coils;
an electrode located on a distal tip of the medical lead, the electrode being electrically coupled to the second coiled portion; and
wherein the electrode being adapted to be electrically coupled to an implantable medical device at a proximal end via the N+M filars of the second coiled portion and the N filar(s) of the first coiled portion.

4. An implantable medical device comprising:
a housing to house circuitry; and
a medical lead electrically coupled to the circuitry, the medical lead including:
  a first coiled portion including N filar(s);
  a second coiled portion electrically coupled to the first coiled portion, the second coiled portion including N+M filars to produce increased stiffness relative to the first coiled portion, wherein N and M are positive integers, wherein the second coiled portion including N+M filars located at a more distal end of the medical lead relative to the first coiled portion;
  wherein the M filar(s) in the second coiled portion form M filar coils in the second coiled portion;
  wherein the N filar(s) in the second coiled portion form N filar coils in the second coiled portion;
  wherein at least one M filar coil in the second coiled portion has a coil diameter that is the same as a coil diameter of at least one of the N filar coils; and
  an electrode located on a distal tip of the medical lead, the electrode being electrically coupled to the second coiled portion; and
an electrically conductive bus to electrically couple the N filar(s) of the first coiled portion to the N+M filars of the second coiled portion.

5. An implantable medical device comprising:
a housing to house circuitry; and
a medical lead electrically coupled to the circuitry, the medical lead including:
  a first coiled portion including N filar(s);
  a second coiled portion electrically coupled to the first coiled portion, the second coiled portion including N+M filars to produce increased stiffness relative to the first coiled portion, wherein N and M are positive integers, wherein the second coiled portion including N+M filars located at a more distal end of the medical lead relative to the first coiled portion;
  wherein the M filar(s) in the second coiled portion form M filar coils in the second coiled portion;
  wherein the N filar(s) in the second coiled portion form N filar coils in the second coiled portion;
  wherein at least one M filar coil in the second coiled portion has a coil diameter that is the same as a coil diameter of at least one of the N filar coils;
  an electrode located on a distal tip of the medical lead, the electrode being electrically coupled to the second coiled portion; and
a weld to electrically couple the M filar(s) of the second coiled portion to the N filar(s) of the first coiled portion, the N filar(s) of the second coiled portion being the same as the N filar(s) of the first coiled portion.

6. A method comprising:
coiling a first set of N filar(s) to define a first portion of a medical lead;
coiling a second set of N+M filars to define a second portion of the medical lead having increased stiffness relative to the first portion, wherein N and M are positive integers and wherein the second portion of the medical lead comprises a more distal portion of the medical lead relative to the first portion, wherein the M filar(s) in the second portion form M filar coils in the second portion, wherein the N filar(s) in the second portion form N filar coils in the second portion, wherein at least one M filar coil in the second portion has a coil diameter that is the same as a coil diameter of at least one of the N filar coils;
electrically coupling the first set of N filar(s) to the second set of N+M filars; and
electrically coupling an electrode on a distal tip of the medical lead to the second set of N+M filars.

7. The method of claim 6, wherein electrically coupling the first set of N filar(s) to the second set of N+M filars includes:
coiling a portion of the first set of N filar(s) around a first end of an electrically conductive bus; and
coiling a portion of the second set of N+M filars around a second end of the electrically conductive bus.

8. The method of claim 6, wherein electrically coupling the first set of N filar(s) to the second set of N+M filars includes welding the M filar(s) to the N filar(s), the N filar(s) of the first set being the same as the N filar(s) of the second set, wherein a weld defines a transition between the first portion and the second portion.

9. A medical lead comprising:
a first coiled portion including N filars extending along a first segment of the lead; and
a second coiled portion electrically coupled to the first coiled portion, the second coiled portion including N+M filars extending along a second segment of the lead, the N+M filars producing increased stiffness of the second coiled portion relative to the first coiled portion, N and M being positive integers, the second coiled portion including N+M filars being located at a more distal end of the medical lead relative to the first coiled portion, the N filars being integrally wound together with M filars such that a N filar being adjacent to a M filar, wherein one or more of the N+M filars of the second coiled portion comprises a different filar diameter than the N filar of the first coiled portion;
wherein the M filar(s) in the second coiled portion form M filar coils in the second coiled portion;
wherein the N filar(s) in the second coiled portion form N filar coils in the second coiled portion;
wherein at least one M filar coil in the second coiled portion has a coil diameter that is the same as a coil diameter of at least one of the N filar coils; and an electrode electrically coupled to the second coiled portion.

10. A medical lead comprising:
a first coiled portion including N filars extending along a first segment of the lead; and
a second coiled portion electrically coupled to the first coiled portion, the second coiled portion including N+M filars extending along a second segment of the lead, the N+M filars producing increased stiffness of the second coiled portion relative to the first coiled portion in which the second coiled portion being distal to the first coiled portion, N and M being positive integers, the second coiled portion including N+M filars being located at a more distal end of the medical lead relative to the first coiled portion,
wherein coils formed by the M filar in the second coiled portion are located between successive pairs of N filar coils in the second coiled portion,
wherein the N filars in the first coiled portion have a different filar diameter as the N filars in the second coiled portion; and
an electrode coupled to the second coiled portion.

11. The medical lead of claim 1, wherein at least one N filar coil and at least one M filar coil of the coils of the N+M filars in the second coiled portion are located on the electrically conductive bus, and wherein the at least one N filar coil and the at least one M filar coil on the electrically conductive bus have the same coil diameter as each other, and wherein the at least one N filar coil and the at least one M filar coil on the electrically conductive bus have a different coil diameter than the coils of the N+M filars of a remainder of the second coiled portion.

* * * * *